(12) United States Patent  
Selkee

(10) Patent No.: US 10,004,417 B2  
(45) Date of Patent: *Jun. 26, 2018

(54) METHOD FOR MAKING A LOW OHMIC PRESSURE-CONTACT ELECTRICAL CONNECTION BETWEEN SPLIT RING ELECTRODE AND LEAD WIRE

(71) Applicant: BIOSENSE WEBSTER (ISRAEL) LTD., Yokneam (IL)

(72) Inventor: Thomas V. Selkee, Claremont, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 63 days.

This patent is subject to a terminal disclaimer.

(21) Appl. No.: 15/063,422

(22) Filed: Mar. 7, 2016

(65) Prior Publication Data

US 2016/0183823 A1    Jun. 30, 2016

Related U.S. Application Data

(63) Continuation of application No. 13/802,259, filed on Mar. 13, 2013, now Pat. No. 9,278,187.

(51) Int. Cl.
*B29C 65/00* (2006.01)
*B32B 37/00* (2006.01)
(Continued)

(52) U.S. Cl.
CPC ............ *A61B 5/042* (2013.01); *A61B 5/6852* (2013.01); *A61B 18/1492* (2013.01);
(Continued)

(58) Field of Classification Search
CPC ........... B29C 66/1122; B29C 66/74285; B29C 66/5221; B29C 66/742; B29C 65/00;
(Continued)

(56) References Cited

U.S. PATENT DOCUMENTS 3,995,623 A    12/1976 Blake et al.
4,444,195 A *  4/1984 Gold ...................... A61N 1/056
                                                600/374
(Continued)

FOREIGN PATENT DOCUMENTS

EP        2 241 279 A1   10/2010
WO        WO 95/22371      8/1995
(Continued)

OTHER PUBLICATIONS

Extended European Search Report dated Aug. 29, 2014 for European patent Application No. EP 14 15 9023 dated by the EPO on Sep. 8, 2014, 7 pgs.
(Continued)

*Primary Examiner* — Philip C Tucker
*Assistant Examiner* — Brian R Slawski
(74) *Attorney, Agent, or Firm* — Lewis Roca Rothgerber Chriistie LLP

(57) ABSTRACT

A method for attaching a split ring electrode to a catheter tip section includes providing a tubing with a lumen and an opening in the tubing side wall, passing an electrode lead wire through the opening, and wrapping the lead wire around the tubing. A split ring electrode is mounted on the tubing over the wrapped lead wire and opening, with electrically-conductive thermoplastic elastomeric adhesive applied between the ring electrode and the outer surface of the tubing, and reheated to reflow.

20 Claims, 7 Drawing Sheets

(51) Int. Cl.
| | |
|---|---|
| *B32B 38/04* | (2006.01) |
| *B32B 7/14* | (2006.01) |
| *B29C 65/48* | (2006.01) |
| *A61B 18/18* | (2006.01) |
| *A61F 7/00* | (2006.01) |
| *A61F 7/12* | (2006.01) |
| *A61F 2/00* | (2006.01) |
| *A61N 1/00* | (2006.01) |
| *A61B 5/00* | (2006.01) |
| *A61B 5/042* | (2006.01) |
| *A61M 25/00* | (2006.01) |
| *A61B 18/14* | (2006.01) |
| *B29C 65/02* | (2006.01) |
| *B29C 65/56* | (2006.01) |
| *B29C 65/72* | (2006.01) |
| *B29C 65/52* | (2006.01) |
| *A61B 17/00* | (2006.01) |
| *A61B 18/00* | (2006.01) |

(52) U.S. Cl.
CPC .............. *A61M 25/0009* (2013.01); *A61B 2017/00526* (2013.01); *A61B 2018/00077* (2013.01); *A61B 2018/00125* (2013.01); *A61B 2018/00136* (2013.01); *A61B 2018/00148* (2013.01); *A61B 2562/0209* (2013.01); *A61B 2562/125* (2013.01); *B29C 65/02* (2013.01); *B29C 65/48* (2013.01); *B29C 65/489* (2013.01); *B29C 65/4815* (2013.01); *B29C 65/4855* (2013.01); *B29C 65/525* (2013.01); *B29C 65/568* (2013.01); *B29C 65/72* (2013.01); *B29C 66/21* (2013.01); *B29C 66/5221* (2013.01); *B29C 66/74285* (2013.01)

(58) Field of Classification Search
CPC ......... B29C 65/02; B29C 65/18; B29C 65/48; B29C 65/4855; B29C 65/489; B29C 66/21; B29C 65/4815; B29C 65/525; B29C 65/567; B29C 65/568; B29C 65/72; C09J 5/06; C09J 11/04; A61B 18/1492; A61B 2018/00577; A61N 1/06; A61N 1/056; A61N 1/403
USPC ........... 156/60, 184, 185, 187, 272.2, 273.7, 156/273.9, 274.4, 276, 290, 291, 293, 156/294, 295, 296; 606/32, 41; 607/99, 607/101, 116, 122; 600/373, 374, 393, 600/395
See application file for complete search history.

(56) References Cited

U.S. PATENT DOCUMENTS

| | | | |
|---|---|---|---|
| 4,592,372 A | 6/1986 | Beranek | |
| 4,718,425 A * | 1/1988 | Tanaka | A61B 5/0215 600/486 |
| 4,922,607 A | 5/1990 | Doan et al. | |
| 4,944,088 A | 7/1990 | Doan et al. | |
| 5,352,315 A | 10/1994 | Carrier et al. | |
| 5,368,037 A * | 11/1994 | Eberle | A61B 8/06 29/25.35 |
| 5,458,629 A * | 10/1995 | Baudino | A61N 1/056 600/396 |
| 5,524,337 A | 6/1996 | Houser et al. | |
| 5,762,770 A | 6/1998 | Pritchard et al. | |
| 6,171,277 B1 | 1/2001 | Ponzi | |
| 6,632,349 B1 | 10/2003 | Hodges et al. | |
| 7,047,082 B1 * | 5/2006 | Schrom | A61N 1/0551 607/116 |
| 7,993,481 B2 | 8/2011 | Hastings et al. | |
| 2001/0016738 A1 * | 8/2001 | Harrington | A61B 17/12022 606/32 |
| 2001/0044645 A1 * | 11/2001 | Hofstad | A61N 1/056 607/122 |
| 2001/9044645 | 11/2001 | Hofstad et al. | |
| 2002/0169444 A1 * | 11/2002 | Mest | A61B 18/1492 606/41 |
| 2005/0097737 A1 | 5/2005 | Webster, Jr. et al. | |
| 2006/0142652 A1 * | 6/2006 | Keenan | A61B 18/1492 600/374 |
| 2007/0088244 A1 * | 4/2007 | Miller | A61B 17/3478 604/21 |
| 2010/0063441 A1 * | 3/2010 | Grunewald | A61B 5/02007 604/95.04 |
| 2010/0217257 A1 | 8/2010 | Howat et al. | |
| 2010/0228202 A1 * | 9/2010 | O'Dea | A61M 25/0013 604/264 |
| 2011/0220408 A1 | 9/2011 | Walsh et al. | |
| 2012/0265186 A1 * | 10/2012 | Burger | A61B 17/8811 606/21 |
| 2013/0220524 A1 * | 8/2013 | Zeroni | A61B 17/32078 156/221 |

FOREIGN PATENT DOCUMENTS

| | | | | |
|---|---|---|---|---|
| WO | WO 2009/001327 A2 | 12/2008 | | |
| WO | WO 2010/135602 A1 | 11/2010 | | |
| WO | WO 2010135602 A1 * | 11/2010 | ......... | A61B 17/8811 |
| WO | WO 2011/005898 A2 | 1/2011 | | |

OTHER PUBLICATIONS

European Examination Report dated Aug. 16, 2017, issued in corresponding EP Application No. 14159023.2, 5 sheets.
Japanese Patent Office Notification of Reasons for Refusal dated Oct. 31, 2017, English language translation, 5 pages.

* cited by examiner

METHOD FOR MAKING A LOW OHMIC PRESSURE-CONTACT ELECTRICAL CONNECTION BETWEEN SPLIT RING ELECTRODE AND LEAD WIRE

CROSS-REFERENCE TO RELATED APPLICATION(S)

This application is a continuation of, and claims priority to and the benefit of, U.S. patent application Ser. No. 13/802,259 filed Mar. 13, 2013, now U.S. Pat. No. 9,278,187, the entire content of which is incorporated herein by reference.

FIELD OF INVENTION

This invention relates to electrophysiology catheters and, in particular, to an improved method for attaching ring electrodes to the tip section of an electrophysiology catheter shaft.

BACKGROUND OF INVENTION

Electrophysiology catheters have been in common use in medical practice for many years. They are used to map and stimulate electrical activity in the heart and to ablate sites of aberrant electrical activity. Among the various types of electrodes used in constructing electrophysiology catheters are ring electrodes. These are metal rings positioned at various intervals along the length of the tip section. The ring electrodes are electrically connected, via electrode lead wires which extend through a lumen in the catheter, to electrical instruments, e.g., a monitor, stimulator or source of energy, e.g., RF energy, for ablation.

A conventional method for making the electrical connection between an electrode lead wire and a ring electrode is to draw the electric lead wire out of a lumen in the tip section through an exit hole that extends from the lumen to the side surface of the shaft of the catheter tip. The distal end of the electrode lead wire, stripped of any non-conductive coating, is then welded or soldered onto the inner surface of a ring electrode. The ring electrode is then slipped over the tip shaft to a position directly over the exit hole while drawing the electrode lead wire back into the lumen. The ring electrode is then secured in place, e.g., by swaging or by the application of an appropriate adhesive. A resin, e.g., polyurethane resin, is often applied to the margins or edges of the ring electrode to assure a smooth transition between the outer circumferential surface of the ring electrode and the outer circumferential surface of the catheter shaft.

Conventional methods for mounting ring electrodes on a catheter have certain drawbacks. For example, because the electrode lead wire must be drawn back into the lumen of the catheter tip section as the ring is slipped over the shaft of the tip section, the exit hole cannot be sealed and visually inspected before the ring electrode is swaged or glued over the exit hole. Further, the ring electrode must have a sufficiently larger diameter than that of the shaft of the catheter tip to slide over the shaft to its final position. Stretching the shaft of the tip section to reduce its diameter is one technique that allows the use of a closer fitting ring electrode. This technique, however, is operator dependent and tends to lead to inconsistent quality in the placement of the ring electrode on the shaft. Further, ring electrodes mounted by the conventional method tend to "pull away" from the shaft of the tip section, i.e., the edge of the ring electrode tends to separate from the surface of the catheter tip shaft along the outside of the curve, during tight bending of the tip section.

Other methods include laser welding, for example, laser melting through a ring electrode to create a laser-welded low ohmic electrical connection to a lead wire. Laser welding however relies on accurate location of the lead wire under the ring electrode during welding. Like conventional resistance welding of ring electrodes, laser welding is manual labor intensive and time-consuming operation that is prone to electrical defects due to improper workmanship methods. Moreover, since catheter tubing is pierced with holes to pass the lead wire from a lumen to outside the tubing, the holes must be made fluid tight after ring placement over the tubing.

Another method is disclosed in US Publication 2005/0097737 A1. Therein, a ring electrode with a flared skirt is swaged to reduce its inner and outer diameter so that it is tightly secured to a tip shaft and makes sufficient pressure contact with underlying electrode lead wire to provide a low ohmic connection. Although the process eliminates ring resistance welding, the low ohmic connections may not be stable long term due to the tendency for stress relaxation of the tubing elastomeric material.

For these and other reasons, there is a need to find a method for attaching ring electrodes to the shaft of the catheter tip section that is less costly, more efficient and does not exhibit the above mentioned drawbacks and disadvantages of the conventional method.

SUMMARY OF THE INVENTION

The present invention provides a method for attaching a ring electrode to the tubing of a catheter tip section. The method comprises providing a tubing with at least one lumen, a side wall and at least one opening in the side wall providing communication between the lumen and outside the tubing. An electrode lead wire is passed through the lumen and out of the opening to expose a distal portion of the electrode lead wire which is positioned or wrapped around on an outer surface of the tubing. A split ring electrode is on the outer surface of the tubing covering the opening and the distal portion of the lead wire, with an electrically-conductive adhesive being provided between the ring electrode and the outer surface of the tubing.

In one embodiment, the electrically-conductive themoplastic elastomeric adhesive is applied as a film on an inner surface of the split ring electrode before mounting on the outer surface of the tubing.

In another embodiment, the electrically-conductive adhesive is applied onto the outer surface of the tubing, covering the opening and at least a portion of the distal portion of the lead wire before mounting the split ring electrode.

In a detailed embodiment, the ring electrode comprises a platinum alloy, for example, an alloy comprising platinum and at least one from the group consisting of iridium, palladium and copper. In a more detailed embodiment, the platinum alloy comprises about 90% platinum.

In a detailed embodiment, the lead wire comprises, stainless steel, copper and/or nickel alloy. The lead wire may comprise a coating of silver, for example a silver flash coating with a thickness ranging between about 20-30 microns. The lead wire may have a diameter ranging between about 0.002 inch and 0.005 inch, and preferably between about 0.002 inch and 0.003 inch. The distal portion of the electrode lead wire may be wrapped about two full turns distally on an outer surface of the tubing.

In a detailed embodiment, the electrically-conductive adhesive comprises an electrically-conductive phase change thermal bonding adhesive, and the method of the present invention includes heating the electrically-conductive adhesive to reflow.

In a detailed embodiment, the split ring electrode has a width ranging between about 1.0 and 3.0 mm and a thickness between 0.001-0.003 inches. The split ring electrode may be constructed of a low cost copper or brass 260 base material with an outer coating of gold, platinum or palladium to prevent oxidization. The thickness of the coating may range between about 10 and 50 microns, and preferably between about 20 and 40 microns.

The method of the present invention may include using a split die assembly with a first and second heated forming die members utilized to radially compress the split ring electrode onto the outer surface of the tubing. Heat may be applied during radial compression to melt the electrically-conductive phase change thermal bonding adhesive so it bonds to both the tubing surface and the lead wires.

The method of the present invention provides many advantages including the following:

1) Much smaller tensile strength lead wires can be used because the wire resistance per unit length is reduced due to a highly conductive (electrically) silver plated outer coating. This allows fitting more lead wires per lumen fixed cross sectional area. Thus higher density electrodes and/or smaller tip French sizes may be utilized with this design.
2) Micro-silver particles in the electrically-conductive adhesive and the silver flash coating on stainless steel, copper or nickel alloy lead wires create a flexible low ohmic electrical connection regardless if silver has oxidized on the lead wires or in the coating. The adhesive is an elastomer so it remains flexible as with the tip section tubing. When the catheter tip section is deflected, no stress is built up between the elastomeric adhesive interface and the tip material and split ring electrode.
3) A unique characteristic of thermal bonding adhesive is its ability to be easily reworked. Merely heating the adhesive past its phase-change temperature (about 250° F.) allows a mounted split ring electrode to be removed or replaced. The adhesive can be heated past its phase=change temperature numerous times allowing for multiple re-works/repairs as necessary. Catheters with failed split ring electrode electrical connection can be repaired without being discarded.
4) Multiple hot melt adhesive coated split rings electrodes can be mounted in a one-step 50 second thermal bonding process. The requirement to slip on a full ring electrode and slide into place on the tubing is eliminated.
5) Method of invention facilitates manufacture of high-density ring electrode catheters where the lead wire diameter is minimized by plating with conductive silver to reduce catheter French size. Silver is one of the most electrically conductive elements even when oxidized. Thus the addition of silver plating on the outside of a low conductivity wire greatly reduces the wire's resistance per unit length.
6) Reflow temperature of electrically conductive thermal bonding adhesive can be adjusted depending on formulation and material melt temperature of tubing for optimizing adhesive bonding and provide ring electrodes that are partially embedded in the tubing material so the ring electrodes are flush with the outer surface of the tubing.
7) Split ring electrodes may be die cut from a large sheet of material and thus they are more economical to manufacture than full ring electrodes.
8) Thermal bonding adhesive and tubing material are both elastomers with similar mechanical properties. During heating and cooling cycles, both have similar expansion coefficients and thus grow and shrink comparably thus maintaining a consistent low ohmic electrical connection.
9) The reflow process of the thermal bonding adhesive makes each split ring electrode self-sealing at the lead wire exit hole.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
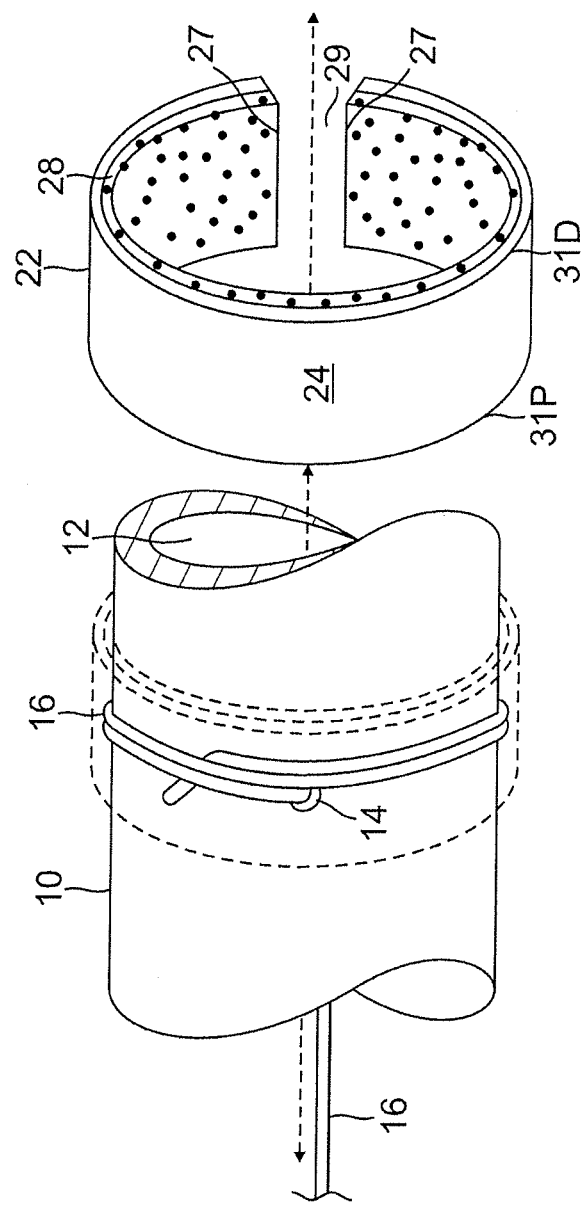
FIG. 1 is a side, exploded view of a portion of a catheter tip section with an exit hole and an electrode lead wire extending out of the exit hole, and a split ring electrode, in accordance with an embodiment of the present invention.

In accordance with the present invention, there is provided an improved method for attaching a split ring electrode to a catheter shaft for making a low ohmic connection to an electrode lead wire using an electrically-conductive adhesive, including an electrically-conductive phase-change thermal bonding adhesive. The method is applicable to catheters of any size and only requires that the body to which the split ring electrode is attached has a generally circular cross-section and at least one lumen therethrough for passage of an electrode lead wire.

The method comprises first providing a distal tip section of a catheter having at least one lumen extending longitudinally through at least a portion of the tip section. The tip section may be the distal portion of an integral, elongated catheter body or may be a separate structure that is attached to the distal end of the catheter body as is well known in the art. See, for example, U.S. Pat. No. 6,171,277, which is incorporated herein by reference. The catheter body and tip section may be made of any material suitable for use in the construction of electrophysiology catheters. Polyurethane is an example of a suitable material.

With reference to FIGS. 1 and 2A-2C, a tubing or shaft 10 of the distal tip section comprises a lumen 12 and a small exit hole 14 that extends between the lumen 12 and the outer side surface of the tubing 10. The size of the exit hole 14 is not critical and can be formed, for example, by inserting a needle through the wall of the tubing 10 and heating the needle sufficiently to form a permanent hole. Such an exit hole is sufficiently large to enable an electrode lead wire 16 to be pulled through the hole, e.g., by a microhook or the like, and yet sufficiently small to be easily sealed.

The electrode lead wire 16 is pulled through the lumen 12 of the tip section 10 and out of the exit hole 14. The length of the electrode lead wire 16 that extends out of the exit hole 14 is not critical, but is sufficient to allow the electrode lead wire 16 to be wrapped around the tubing 10 of the tip section 10 a desired number of turn(s). The electrode lead wire 16 may be made of any suitable, preferably non-oxidizing, material and may have any suitable diameter. In one embodiment, the electrode lead wire is about 0.002 inch diameter wire of stainless steel, copper and/or a nickel alloy, for example, a nickel alloy comprising up to about 67% nickel, with the remainder being copper, iron and/or other trace elements. A suitable nickel alloy is MONEL 400 binary alloy of equal proportions of nickel and copper, available from Special Metals Corporation of New Hartford, N.Y. In a preferred embodiment, a MONEL 400 lead wire has a flash coating of silver of a thickness ranging between about 20-30 microns.

The portion of the electrode lead wire 16 that extends out of the exit hole 14 is stripped of insulation and wrapped around the tubing 10. A particularly preferred wrapping technique is shown in FIG. 1. In this technique, the electrode lead wire 16 extending from the exit hole 14 is wrapped around the tubing 10 in one direction for two full turns, with the two turns proceeding in a distal direction. The free end of the electrode lead wire 16 is passed under the two wraps in a clove hitch arrangement, as shown. After wrapping, the free end of the electrode lead wire 16 is pulled to eliminate any slack in the wraps. Distal end of the lead wire 16 is trimmed adjacent to the lead wire wrap.

Figure 3A:
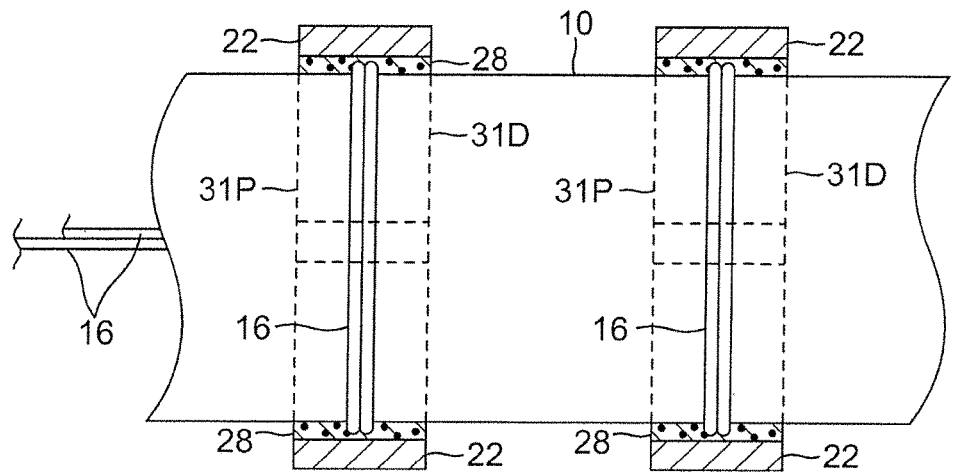
FIG. 3A is an opposing side view of the catheter tip section of FIG. 2A, with the mounted split ring electrode partially broken away.
Figure 3B:
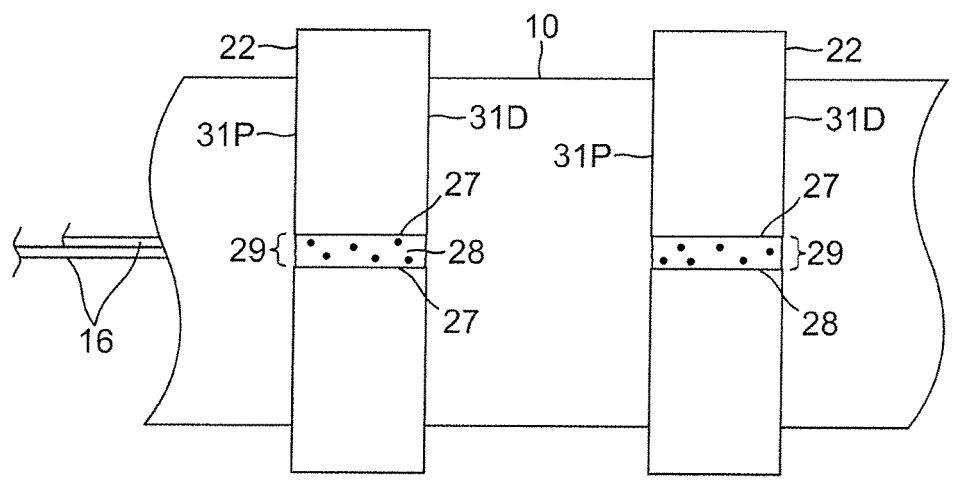
FIG. 3B is a side view of the catheter tip section of FIG. 3A, with no parts broken away.

With additional reference to FIGS. 3A and 3B, a split ring electrode 22 is provided which has an inner diameter slightly greater than the outer diameter of the tubing 10 to allow it to be slipped over the tubing 10 to a location over the wrapped electrode lead wire 16 and exit hole 14. For example, if the tubing 10 has an outer diameter of 0.084 inch, a ring electrode 22 having an inner diameter of 0.085 inch is preferred.

Figure 4:
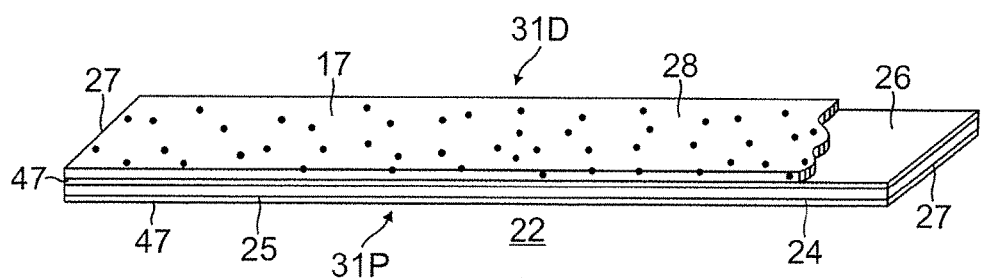
FIG. 4 is a perspective view of an split ring electrode in its initial form prior to mounting.

As shown in FIG. 4, the ring electrode 22 is formed from an elongated rectangular planar piece of material 25 with an outer surface 24 and an inner surface 26 an two opposing ends 27. The ring electrode may be made of any suitable, conductive, preferably non-oxidizing, material. One preferred material is a platinum-based alloy including iridium and/or palladium. In one embodiment, the alloy includes about 90% platinum, with the remainder being iridium and/or palladium. The alloy has a width ranging between about 1.0 and 3.0 mm. If a non-noble metal is used as the base material (copper or brass 260) for the split ring electrode, a plating 47 of gold or palladium with a thickness ranging between about 10 and 40 microns is provided on the inner and outer surfaces 24 and 26. Polyurethane adhesive may be used to coat and seal both distal and proximal circumferential edges 31D and 31P (FIG. 4).

On the inner surface 26 the ring electrode 22 has a coating of an electrically-conductive adhesive 17, including an electrically-conductive-phase-change thermal bonding adhesive in film form 28. A suitable adhesive is FASTELEK available from Fastel Adhesives, San Clemente, Calif. FASTELEK is an electrically conductive EVA-based solvent free (metallic filled) adhesive that is available as a film and designed to provide low resistance electrical conductivity, uniform adhesion and sealing across a desired material interface. FASTELEK is available in multiple fillers (silver, nickel or gold), thicknesses and phase-change (melt point) temperatures. FASTELEK is an elastomeric adhesive with about a shore 80-90 A hardness and 150% tensile elongation before failure and is designed to adhere strongly to a wide range of metals, plastics and elastomers.

The ring electrode 22 is positioned over the wrapped lead wire 16 with the outer surface 24 facing away from the tubing 10 and the thermal bonding adhesive film 28 facing the wrapped lead wire 16, with a length dimension of the ring electrode generally perpendicular to the longitudinal axis of the tubing 10. Heat and a circumferentially-compressive force are applied to wrap, adhere, mount and electrically connect the ring electrode 22 around the tubing 10. The ring electrode 22 covers the wrapped lead wire 16 with the wrapped lead wire being generally centered under the ring electrode. Mounted on the tubing 10, the ring electrode adopts a C cross-sectional shape with the ends 27 approaching each other around the tubing 10 forming a split or gap 29 in the C-shape. Notably, the ring electrode 22 is oriented on the tubing 10 such that the split 29 avoids the exit hole 14 where the lead wire 16 exits the lumen 12. In the illustrated embodiment, the split 29 and the exit hole 14 are diametrically opposite of each other.

With the application of heat, the thermal bonding adhesive film 28 begins its controlled flow when cycled past its phase-change temperature and bonds to the silver flash-plated lead wire 16 under the ring electrode 22 and filling in and adjusting any microscopic surface conditions or irregularities that may exist on the outer surface of the tubing 10. As such, the adhesive film 28 reflows to seal voids and air gaps between the ring electrode 22 and outer surface of the tubing 10, including the hole 14 sealing it and protecting the lumen 12 from contamination that can otherwise enter the lumen 12 through the hole 14. The adhesive film 28 also reflows to seal circumferential edges on distal and proximal edges 31D and 31P of the ring electrode 22. The adhesive film 28 further flows into the gap 29 thereby sealing transverse edges at ends 27.

The film 28 may be produced by heating the adhesive to flow onto a large sheet of foil, with a thickness of 0.0007 inch, and die cut from the large sheet of foil. During the mounting of the split ring electrode 22 to the tube 10, the adhesive film 28 is reheated for reflowing to attach it to the tubing and lead wire.

Figure 2A:
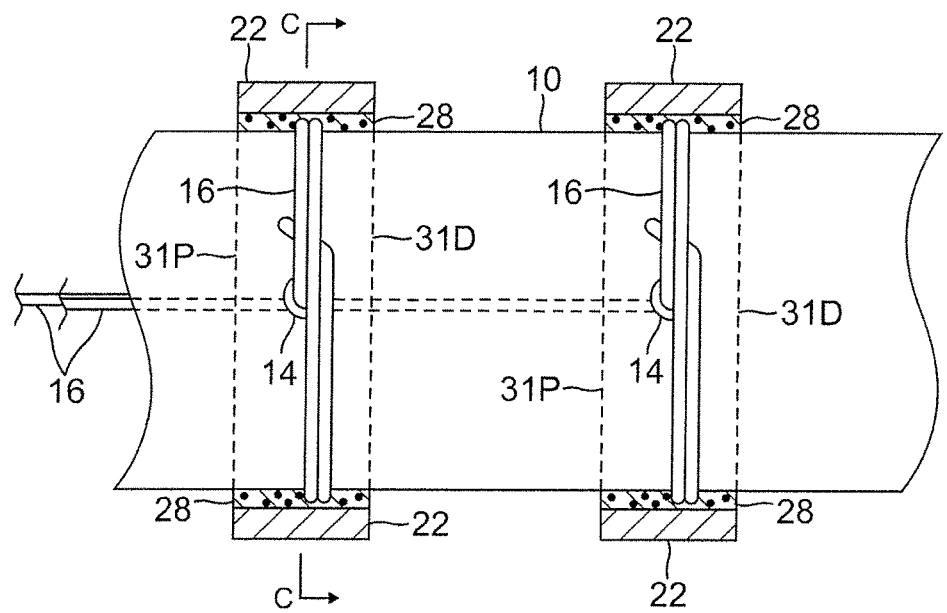
FIG. 2A is a side view of a catheter tip section with a mounted split ring electrode partially broken away, in accordance with an embodiment of the present invention.
Figure 2B:
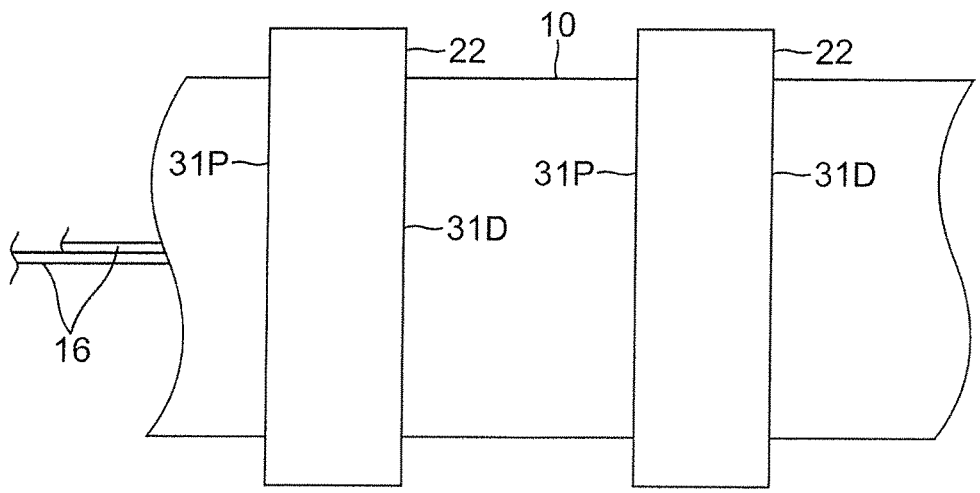
FIG. 2B is a side view of the catheter tip of FIG. 2A, with no parts broken away.
Figure 2C:
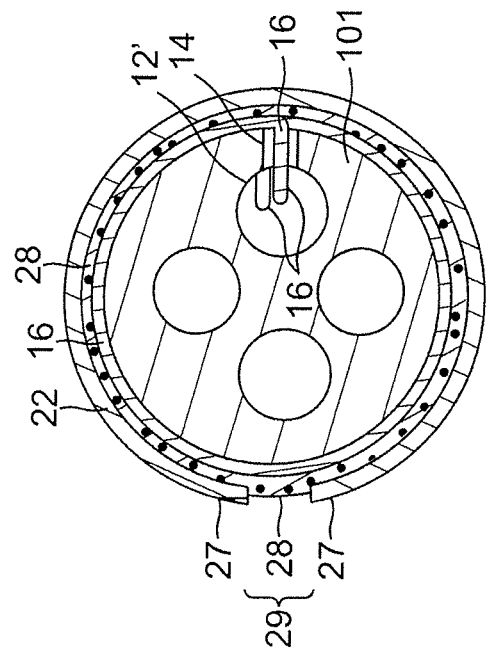
FIG. 2C is an end cross-sectional view of the catheter tip section of FIG. 2A, taken along line C-C.
Figure 2D:
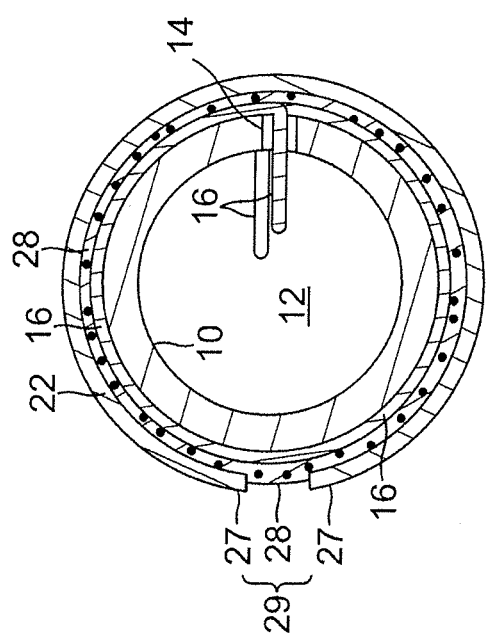
FIG. 2D is an end cross-sectional view of a catheter tip section with a multi-lumened tubing, in accordance with an embodiment of the present invention.

As illustrated in FIG. 2C, the distal tip section 15 manufactured in accordance with the present invention has a C-shaped split ring electrode 22 mounted on the tubing 10 which has the lumen 12 and the opening 14 through which the lead wire 16 passes from the lumen 12 to an outer surface of the tubing around which a distal portion of the lead wire is wrapped. The split ring electrode 22 and the lead wire 16 are electrically connected by the thermal bonding adhesive film 28 between an outer surface of the tubing 10 and the ring electrode 22 which is mounted on the tubing 10 covering the wrapped lead wire 16. The electrical connection is advantageously accomplished without resistance welding or laser welding. Accordingly, manufacture of a distal tip section 15 under the present invention is less manual-labor intensive, less time-consuming and less prone to electrical defects due to improper workmanship methods. It is understood that the present invention includes the use of a multi-lumened tubing 10' as shown in FIG. 2D, where the lead wires 16 extend through a lumen 12' in communication with the openings 14.

Figure 5:
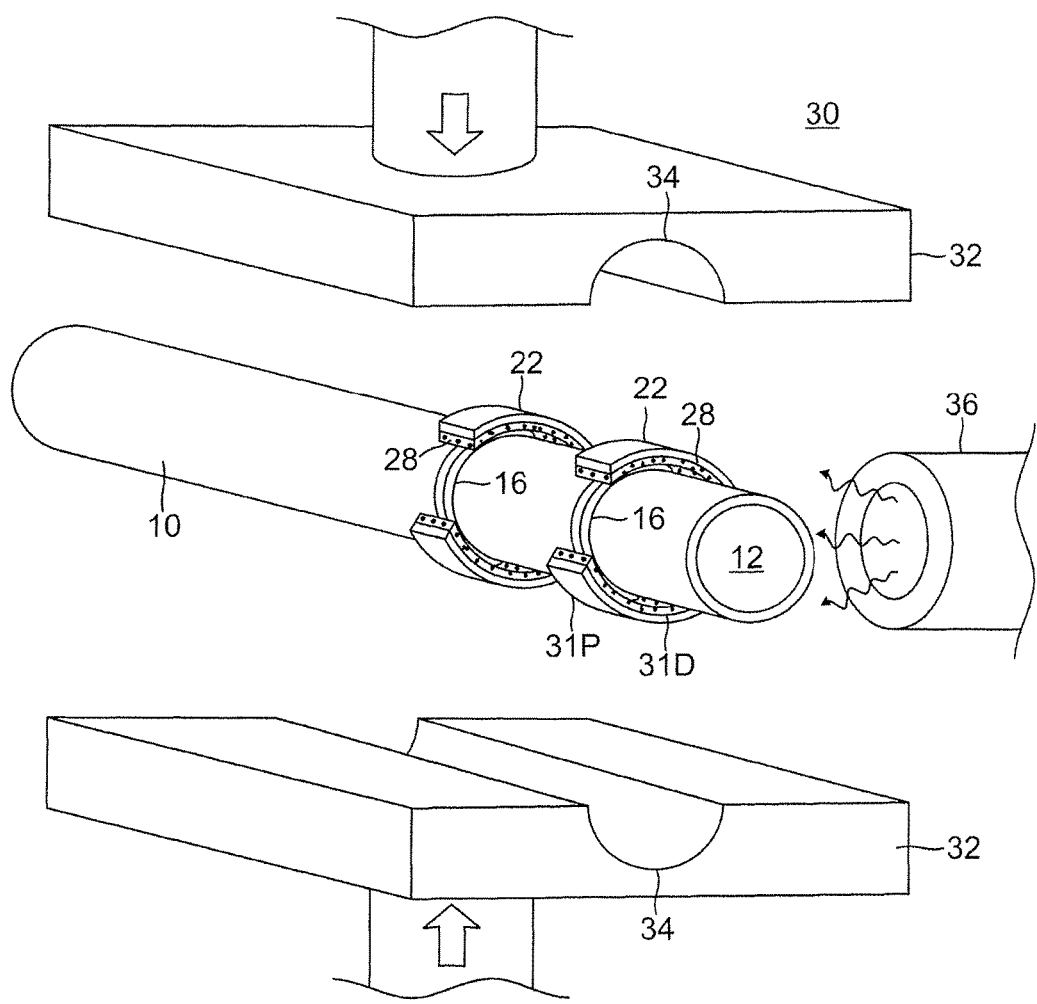
FIG. 5 is a schematic perspective view of a die assembly in use on one embodiment of a catheter tip section in accordance with a feature of the present invention.

Once the ring electrode 22 has been positioned directly over the wrapped lead wire 16, the distal tip section 15 (and any other portion of the catheter carrying split ring electrodes) is placed in a die assembly 30, as shown in FIG. 5. Each of movable upper and lower semi-circular shaped die half members 32 has semi-cylindrical recessed form 34 which jointly form a full cylindrical form with a diameter that defines the desired outer diameter size for the distal tip section 15 (and any other portion of the catheter carrying split ring electrodes). Each of the upper and lower die members 32 may be heated so as to melt and reflow the thermal bonding adhesive film 28 which allows the reflowed adhesive to bond with the wrapped lead wire 16 and ring electrode 22 and tubing 10. The die members 32 may be heated by any conventional methods, e.g., it may be heated by an electric heating element. Alternatively or in addition, hot air may be supplied by a tube or pipe 36 as shown. As described above, the reflowed adhesive also fills in microscopic surface conditions, adjusts for any surface irregularities in the tubing 10 outside diameter, fills in the exit hole 14 and seals proximal and distal circumferential edges of the ring electrodes.

Accordingly, the reflowed adhesive forms electrically conductive low-ohmic connection between the split ring electrodes 22 and their respective lead wires 16. To that end, the silver coating on the lead wires 16 greatly reduces the lead wire resistance per linear unit length where both lead wires 16 and thermal bonding adhesive contain silver which has the highest conductivity of any element, a flexible low ohm connection is established without any mechanical stresses introduced in the ring electrodes 22 or tubing 10. The split ring electrodes 22 mounted in accordance with the present invention also has the benefit of reduced resistance between the ring electrode 22 and connector pins (not shown) in a catheter control handle 16 by about 50% compared to existing catheters using MONEL lead wires. MONEL 400 wire at 0.003 inches in diameter has a resistance of 40 ohms per foot and flash silver plated MONEL 400 at 0.002 inches in diameter has a reduced resistance of 20 ohms per foot. Accordingly, the present invention facilitates the manufacture of very economical, high-density electrode catheters since all ring electrodes can be located on the distal tip section and electrically connected to lead wires in a single operation and MONEL lead wires with flash silver coating can be made in smaller diameters while decreasing the overall ring electrode to connector pin resistance. The number of lead wires (e.g., from 1 to 50+) that be fed through a lumen can also be increased.

It is understood that the local area of the tubing 10 adjacent the wrapped lead wires is heated while the distal tip section 15 is in the die assembly. Where the tubing is of polyurethane, a temperature between about 110-125 C also softens material of tubing. This softening may help to embed the wrapped lead wires into the outer surface of the tubing so as to allow the die assembly to further minimize the outer diameter of the ring electrode as mounted on the tubing over the wrapped lead wires.

It is understood that, while heating to facilitate embedding of the wire wraps is preferred, it is not necessary to practice the invention. Moreover, when heating is used, any temperature that softens the plastic material of the shaft of the tip section may be employed. Further, any technique or device that allows heating, particularly localized heating, may be used.

Figure 6:
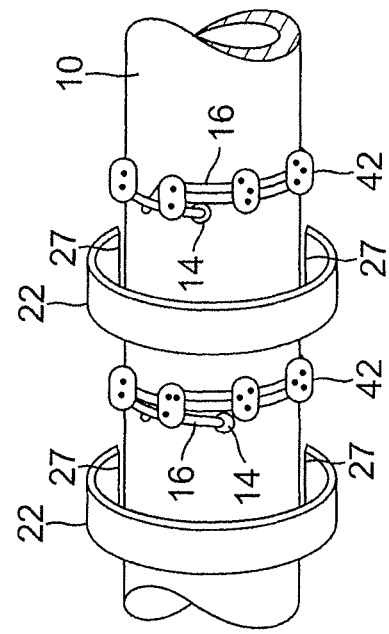
FIG. 6 is a schematic perspective view of a dispensing needle applying adhesive to a catheter tip section in accordance with an embodiment of the present invention.
Figure 7:
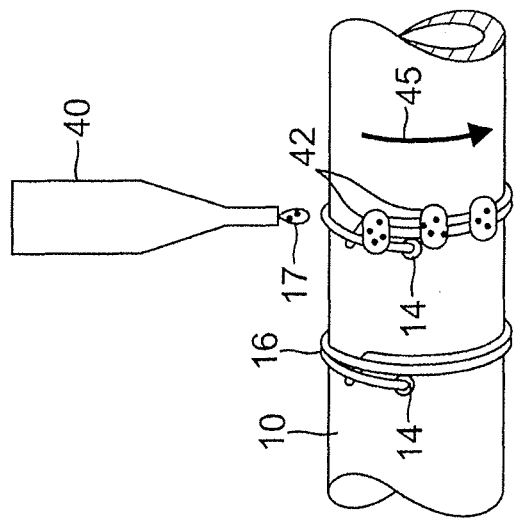
FIG. 7 is a side view of the catheter tip section of FIG. 6 prepared for mounting of split ring electrodes.
Figure 8:
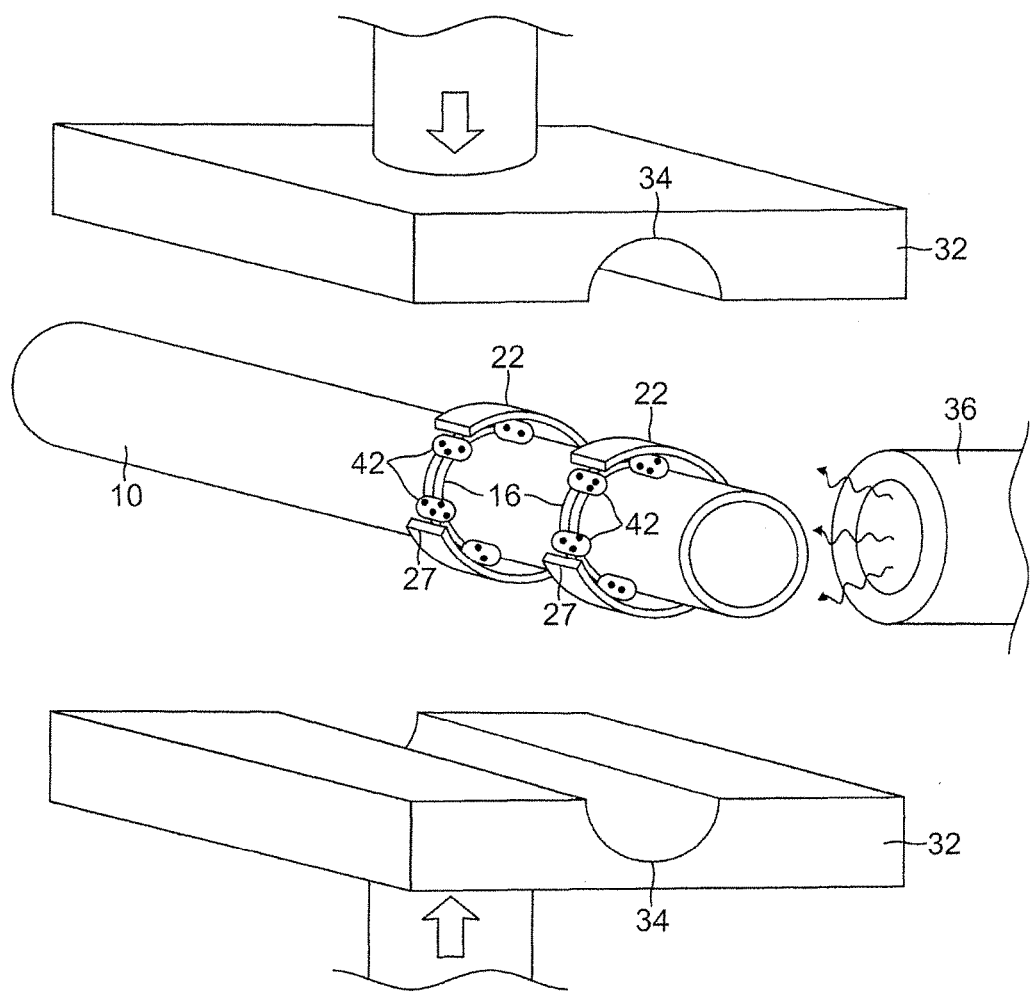
FIG. 8 is a schematic perspective view of a die assembly in use on another embodiment of a catheter tip section in accordance with the present invention.

An alternative method of manufacture in accordance with the present invention is illustrated in FIGS. 6-8. The tubing 10 is prepared with exit holes 14 and lead wires 16 wrapped around the outer surface of the tubing, as described above. The prepared tubing is then positioned under a dispensing needle 40 dispensing the thermal bond adhesive 17 directly on the outer surface of the tubing 10 and the wrapped lead wires 16 as the tubing 10 is rotated axially as shown by the arrow 45. The adhesive may be applied as a continuous line or as individual beads 42. The dispenser needle 40 is heated, e.g., by an electric heating element, to melt and reflow the adhesive 17, or hot air may be provided via tube or pipe 36. A split ring electrode 22 (with or without a thermal bond adhesive film) is then mounted on the tubing 10 to cover the applied adhesive 42 and the wrapped lead wire 16 by means of the die assembly 30.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the advancing wire control mechanism may be integrated anywhere along the control handle. User interface may be modified to allow for a linear motion deflection knob rather than the rotational knob mentioned above. If bi-directional deflection is desired, a second puller wire may be provided, as understood by one of ordinary skill in the art. Moreover, the drawings are not necessarily to scale.

Accordingly, the foregoing description should not be read as pertaining only to the precise structures described and illustrated in the accompanying drawings, but rather should be read consistent with and as support to the following claims which are to have their fullest and fair scope.

What is claimed is:
1. A method for attaching a split ring electrode to a tubing of a catheter, comprising:
   providing a tubing with at least one lumen, a side wall and at least one opening in the side wall providing communication between the at least one lumen and outside the tubing;
   passing an electrode lead wire through the at least one lumen and out of the at least one opening to expose a distal portion of the electrode lead wire;
   positioning the distal portion of the electrode lead wire on an outer surface of the tubing;
   dispensing an electrically conductive adhesive on the outer surface of the tubing from a dispenser housing the electrically conductive adhesive by rotating the tubing underneath the dispenser while the dispenser dispenses the electrically conductive adhesive; and mounting a split ring electrode on the outer surface of the tubing covering the opening, the distal portion of the electrode lead wire and the electrically conductive adhesive; and heating the electrically-conductive adhesive to reflow.

2. The method of claim 1, wherein the split ring electrode comprises a platinum alloy.

3. The method of claim 2, wherein the platinum alloy comprises platinum and at least one selected from the group consisting of iridium, palladium and copper.

4. The method of claim 2, wherein the platinum alloy comprises about 90% platinum.

5. The method of claim 1, wherein the electrode lead wire comprises, stainless steel, copper and/or nickel alloy.

6. The method of claim 1, wherein the electrode lead wire comprises a coating of silver.

7. The method of claim 6, wherein the coating of silver has a thickness ranging between about 20-30 microns.

8. The method of claim 1, wherein the electrode lead wire has a diameter ranging between about 0.002 inch and 0.005 inch.

9. The method of claim 1, wherein the dispensing the electrically-conductive adhesive includes dispensing the electrically-conductive adhesive from the dispenser in intervals so that the electrically-conductive adhesive is provided on spaced apart portions of the distal portion of the electrode lead wire and the outer surface of the tubing.

10. The method of claim 1, wherein the dispensing the electrically-conductive adhesive comprises dispensing a generally continuous line of the electrically-conductive adhesive from the dispenser circumferentially around the tubing.

11. The method of claim 1, wherein the dispensing the electrically-conductive adhesive comprises dispensing individual beads of the electrically-conductive adhesive circumferentially around the tubing.

12. The method of claim 1, wherein positioning the distal portion of the electrode lead wire on an outer surface of the tubing includes wrapping the distal portion around the outer surface of the tubing.

13. The method of claim 1, wherein the electrically-conductive adhesive comprises an electrically-conductive phase change thermal bonding adhesive.

14. The method of claim 1, wherein the heating the electrically-conductive adhesive to reflow comprises either:

heating the dispenser during the dispensing, or heating the electrically-conductive adhesive after the dispensing and after the mounting the split ring electrode.

15. The method of claim 1, wherein the split ring electrode has a width ranging between about 1.0 and 3.0 mm.

16. The method of claim 1, wherein the split ring electrode has a coating of gold or palladium.

17. The method of claim 16, wherein the coating on the split ring electrode has a thickness ranging between about 10 and 40 microns.

18. The method of claim 1, wherein the mounting the split ring electrode on the outer surface of the tubing comprises radially compressing the split ring electrode onto the outer surface of the tubing.

19. The method of claim 1, wherein the mounting the split ring electrode on the outer surface of the tubing comprises radially compressing the split ring electrode onto the outer surface of the tubing and heating the electrically-conductive adhesive.

20. A method for attaching a split ring electrode to a tubing of a catheter, comprising:

providing a tubing with at least one lumen, a side wall and at least one opening in the side wall providing communication between the at least one lumen and outside the tubing;

passing an electrode lead wire through the at least one lumen and out of the at least one opening to expose a distal portion of the electrode lead wire;

positioning the distal portion of the electrode lead wire on an outer surface of the tubing;

mounting a split ring electrode on the outer surface of the tubing covering the at least one opening and the distal portion of the electrode lead wire;

providing an electrically-conductive adhesive between the split ring electrode and the outer surface of the tubing; and heating the electrically-conductive adhesive to reflow.

* * * * *